United States Patent
Nakamura et al.

[11] Patent Number: 5,965,492
[45] Date of Patent: Oct. 12, 1999

[54] TRIKETONE DERIVATIVES

[75] Inventors: Kazufumi Nakamura, Chita; Mitsuru Shibata, Chiba; Kazuyoshi Koike, Ichihara, all of Japan

[73] Assignee: Idemitsu Kosan Co., Ltd., Tokyo, Japan

[21] Appl. No.: 08/981,407

[22] PCT Filed: Jul. 5, 1996

[86] PCT No.: PCT/JP96/01873

§ 371 Date: Dec. 19, 1997

§ 102(e) Date: Dec. 19, 1997

[87] PCT Pub. No.: WO97/03064

PCT Pub. Date: Jan. 30, 1997

[30] Foreign Application Priority Data

Jul. 12, 1995 [JP] Japan .................................. 7-175729

[51] Int. Cl.⁶ .................................................... A01N 43/16
[52] U.S. Cl. ........................................... 504/288; 549/23
[58] Field of Search .................... 549/292, 23; 568/327; 504/288

[56] References Cited

U.S. PATENT DOCUMENTS 5,468,878  11/1995  Nasuno et al. .......................... 549/23
5,480,858  1/1996  Sakamoto et al. ....................... 504/288

*Primary Examiner*—John Kight
*Assistant Examiner*—Raymond Covington
*Attorney, Agent, or Firm*—Frishauf, Holtz, Goodman, Langer & Chick

[57] ABSTRACT

A triketone compound of the following formula:

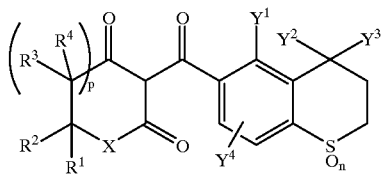

wherein $Y^1$ is $C_1$ to $C_4$ alkyl, a halogen or a $C_1$ to $C_4$ haloalkyl; each of $Y^2$ and $Y^3$ is independently $C_1$ to $C_4$ alkyl; $Y^4$ is hydrogen, $C_1$ to $C_4$ alkyl or a halogen; n is 0, 1 or 2; p is 0 or 1; each of $R^1$, $R^2$, $R^3$ and $R^4$ is independently hydrogen, $C_1$ to $C_4$ alkyl or phenyl; or when p is 1, either $R^1$ or $R^2$ and either $R^3$ or $R^4$ optionally bond to each other to form an intramolecular double bond; and X is oxygen or sulfur. The triketone compound is useful as a herbicide to control a broad range of upland weeds at a low dosage without causing phytotoxicity on corn.

16 Claims, No Drawings

TRIKETONE DERIVATIVES

TECHNICAL FIELD

The present invention relates to a triketone derivative and a herbicide containing the same.

BACKGROUND ART

Herbicides are very important chemicals for labor-saving of weed control and improving the productivity of agricultural and horticultural crops. Herbicides have been therefore actively studied and developed for many years, and a variety of herbicides are practically used. However, it is still desired today to develop novel chemicals having further prominent herbicidal properties, particularly chemicals which can selectively control target weeds alone without causing phytotoxicity on cultivated crops and which can also control them at a low dosage.

During a planting time of corn, etc., triazine-based herbicides such as atrazine and acid anilide-based herbicides such as alachlor and metolachlor have been conventionally used. However, atrazine shows low efficacy to gramineous weeds, and on the other hand, alachlor and metolachlor show low efficacy to broad-leaved weeds. It is therefore difficult at present to control gramineous weeds and broad-leaved weeds together simultaneously with a single herbicide. Further, the above herbicides are undesirable in view of an environmental problem due to their high dosage requirement.

In view of the above circumstances, the present inventors have invented novel triketone derivatives having a thiochroman ring and filed a patent application therefor (International Patent Application WO94/04524). A typical example disclosed in this Publication is as follows.

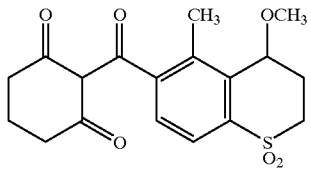

However, the above compound is not fully satisfactory in soil treatment activity although it is free of phytotoxicity on corn and has high foliar treatment activity.

DISCLOSURE OF INVENTION

It is an object of the present invention to provide a triketone derivative which can control a broad range of upland weeds at a low dosage without causing phytotoxicity on crops such as corn, etc.

The present inventors have made diligent studies to achieve the above object, and as a result, have found that a novel triketone derivative of the following general formula (I) can control a broad range of upland weeds at a low dosage without causing phytotoxicity on crops such as corn, etc. The present invention has been accordingly completed.

The present invention is directed to
(1) a triketone derivative of the general formula,

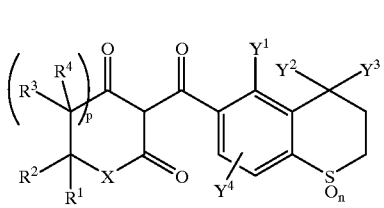

(I)

wherein:
$Y^1$ is a $C_1$~$C_4$ alkyl group, a halogen atom or a $C_1$~$C_4$ haloalkyl group,
each of $Y^2$ and $Y^3$ is independently a $C_1$~$C_4$ alkyl group,
$Y^4$ is a hydrogen atom, a $C_1$~$C_4$ alkyl group or a halogen atom,
n is an integer of 0, 1 or 2,
p is 0 or 1,
each of $R^1$, $R^2$, $R^3$ and $R^4$ is independently a hydrogen atom, a $C_{1~4}$ alkyl group or a phenyl group, or when p is 1, either $R^1$ or $R^2$ and either $R^3$ or $R^4$ may bond to each other to form an intramolecular double bond, and
X is an atom of oxygen family or a group of

(in which each of $R^5$ and $R^6$ is independently a hydrogen atom, a $C_1$~$C_4$ alkyl group or a phenyl group), and
(2) a herbicide containing the triketone derivative of the above general formula (I) as an active ingredient.

PREFERRED EMBODIMENTS FOR PRACTICING INVENTION

First, the triketone derivative of the present invention will be explained.

The triketone derivative of the present invention has the general formula (I).

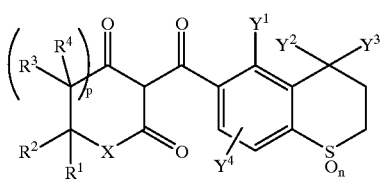

(I)

In the above general formula (I), $Y^1$ is a $C_1$~$C_4$ alkyl group, a halogen atom or a $C_1$~$C_4$ haloalkyl group. The $C_1$~$C_4$ alkyl group includes methyl, ethyl, propyl groups such as n-propyl and i-propyl, and butyl groups such as n-butyl and i-butyl. Methyl is preferred. The halogen atom includes fluorine, chlorine, bromine and iodine atoms. The $C_1$~$C_4$ haloalkyl group includes —$CH_2Cl$, —$CHCl_2$, —$CCl_3$, —$CCl_2CH_3$, —$CH_2F$, —$CHF_2$, —$CF_3$, —$CF_2CH_3$, —$CH_2CH_2F$, —$CF_2CF_3$, —$CH_2CH_2CHF_2$, —$CH_2CH_2CH_2CH_2F$, $CH_2CH_2CHCl_2$, —$CH_2CH_2CH_2CH_2Cl$, —$CH(CH_3)$ $CH_2F$, —$CH(C_2H_5)$ $CH_2F$, and $-CH(CH_3)CH_2Cl$. $Y^1$ is preferably methyl, a chlorine atom or $-CF_3$, particularly preferably methyl.

Each of $Y^2$ and $Y^3$ is independently a $C_1\sim C_4$ alkyl group. Specific examples of the $C_1\sim C_4$ alkyl group are those described in the explanation of $Y^1$, and methyl is preferred.

$Y^4$ is a hydrogen atom, a $C_1\sim C_4$ alkyl group or a halogen atom. Specific examples of the $C_1\sim C_4$ alkyl group and the halogen atom are those described in the explanation of $Y^1$. $Y^4$ is preferably a hydrogen atom, methyl or a fluorine atom, particularly preferably, methyl. When $Y^4$ is a $C_1\sim C_4$ alkyl group or a halogen atom, $Y^4$ can bond to the 7- or 8-position on the thiochroman ring, while, preferably, $Y^4$ bonds to the 8-position.

in which each of $R^5$ and $R^6$ is independently a hydrogen atom or methyl.

The triketone derivative of the general formula (I) may have the following four structures due to tautomerism, and the triketone derivative of the present invention includes all of these four structures.

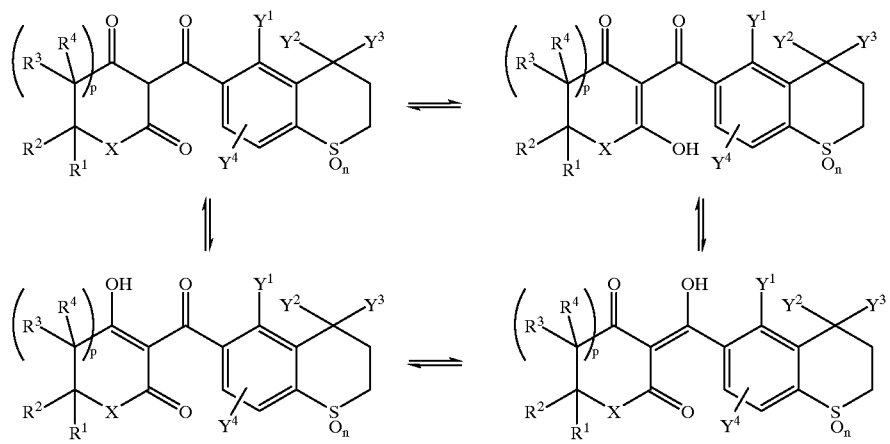

n represents the number of oxygen atom(s) bonding to a sulfur atom, and n is an integer of 0, 1 or 2. When n=0, a sulfide is represented. When n=1, a sulfoxide is represented. When n=2, a sulfone is represented.

p is 0 or 1. A (hetero)cyclodiketone ring bonding to the thiochroman ring is a 5-membered ring when p=0 or a six-membered ring when p=1.

Each of $R^1$, $R^2$, $R^3$ and $R^4$ is independently a hydrogen atom, a $C_1\sim C_4$ alkyl group or a phenyl group. Specific examples of the $C_1C\sim_4$ alkyl group are those described in the explanation of $Y^1$. Further, when p is 1, either $R^1$ or $R^2$ and either $R^3$ or $R^4$ may bond to form a double bond in the molecule. Preferably, each of $R^1$, $R^2$, $R^3$ and $R^4$ is independently a hydrogen atom, methyl, 1-propyl or a phenyl group, or p is 1 and either $R^1$ or $R^2$ and either $R^3$ or $R^4$ bond to form a double bond in the molecule.

X is an atom of the oxygen family or a group of

The atom of the oxygen family includes oxygen and sulfur atoms. In the above formula showing an alkylidene group, each of $R^5$ and $R^6$ is independently a hydrogen atom, a $C_1\sim C_4$ alkyl group or a phenyl group. Specific examples of the $C_1\sim C_4$ alkyl group are those described in the explanation of $Y^1$. X is preferably an oxygen atom or a group of (wherein $Y^1$, $Y^2$, $Y^3$, $Y^4$, n, p, $R^1$, $R^2$, $R^3$, $R^4$ and X are as defined above).

The triketone derivative of the general formula (I) is an acidic substance, and can be easily converted to a salt by treating it with a base. This salt is also included in the triketone derivative of the present invention. The base can be selected from known bases without any limitation. For example, the base includes organic bases such as amines and anilines and inorganic bases such as a sodium compound and a potassium compound. The amines include a monoalkylamine, a dialkylamine and a trialkylamine. The alkyl group of each of the alkylamines is generally a $C_1\sim C_4$ alkyl group. The anilines include aniline, a monoalkylaniline and a dialkylaniline. The alkyl group of each of the alkylanilines is generally a $C_1\sim C_4$ alkyl group. The sodium compound includes sodium hydroxide and sodium carbonate. The potassium compound includes potassium hydroxide and potassium carbonate.

The triketone derivative of the general formula (I) is produced by the following method.

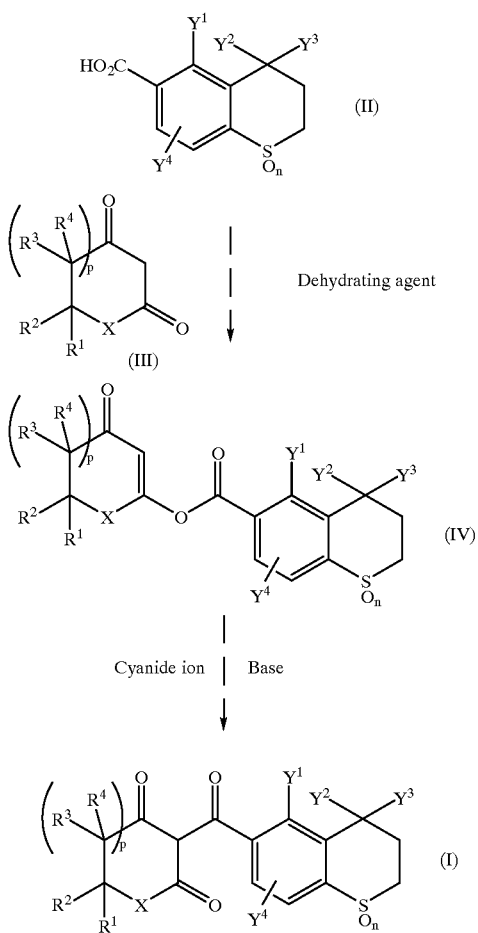

(wherein $Y^1$, $Y^2$, $Y^3$, $Y^4$, n, p, $R^1$, $R^2$, $R^3$, $R^4$ and X are as defined above).

That is, a compound of the general formula (II) is reacted with a compound of the general formula (III) in the presence of a dicyclohexylcarbodiimide (to be referred to as "DCC" hereinafter), and then the reaction product is rearranged to obtain the triketone derivative of the general formula (I) as an end product. During the reaction, an ester compound of the general formula (IV) is formed as an intermediate. The intermediate may be isolated, while it is preferred to use the intermediate in the rearrangement reaction without isolating it.

The solvent used for a condensing reaction between the compound (II) and the compound (III) is not specially limited so long as it is inert to the reaction, while it is preferred to use acetonitrile or tertiary amyl alcohol. The reaction temperature is not specially limited so long as it is in the range of from 0° C. to the boiling point of the solvent. The reaction temperature is preferably room temperature. The dehydrating agent includes 1,1-carbonyl diimidazole (CDI) and a 1-(3-dimethylaminopropyl)-3-ethylcarbodiimide (EDC) in addition to the above DCC. The amount of the dehydrating agent based on the compound (II) is 1.0 to 3.0 equivalent weights, preferably 1.0 to 1.5 equivalent weights. The compound (II):compound (III) amount ratio by mole is in the range of 1:1~1:3, preferably 1:1~1:1.5. The condensing reaction between the compound (II) and the compound (III) is 1 to 48 hours, while it is generally completed approximately in 8 hours.

The rearrangement reaction is accomplished by reacting a cyanide ion with the compound (IV) in the presence of a base. The base is selected from sodium carbonate, potassium carbonate, triethylamine and pyridine. It is preferred to use a base in an amount of 1 to 2 equivalent weights based on the compound (IV). The cyanide which produces a free cyanide ion an alkali metal cyanide and cyanohydrin compounds such as acetone cyanohydrin. The cyanide is used in an amount of 0.05 to 0.5 mole equivalent based on the compound (IV). The rearrangement reaction can be smoothly proceeded with by adding a phase transfer catalyst such as a crown ether compound. The reaction temperature is not specially limited so long as it is in the range of 0° C. to the boiling point of the solvent. The reaction temperature is generally preferably room temperature. The rearrangement is accomplished in 1 to 72 hours, while it is generally completed approximately in 8 hours.

The compound of the general formula (II) as a starting material can be obtained by the method disclosed in International Laid-open Publication No. WO95/04054. Most of compounds of the general formula (III) are known or can be produced by a known method.

The herbicide of the present invention will be explained hereinafter.

The herbicide of the present invention contains, as an active ingredient, the novel triketone derivative of the general formula (I) and/or its salt, provided by the present invention. When these compounds are used, they are mixed with a liquid carrier such as a solvent or a solid carrier such as a mineral fine powder and the mixtures are prepared into preparations in the form of a wettable powder, an emulsifiable concentrate, a dust or granules. These compounds can be imparted with emulsifiability, dispersibility or spreadability by adding a surfactant when the above preparations are formed.

When the herbicide of the present invention is used in the form of a wettable powder, generally, 10 to 55% by weight of the triketone derivative and/or the salt thereof, provided by the present invention, 40 to 88% by weight of a solid carrier and 2 to 5% by weight of a surfactant are mixed to prepare a composition, and the composition can be used. When the herbicide of the present invention is used in the form of an emulsifiable concentrate, generally, the emulsifiable concentrate can be prepared by mixing 20 to 50% by weight of the triketone derivative and/or the salt thereof, provided by the present invention, 35 to 75% by weight of a solvent and 5 to 15% by weight of a surfactant.

When the herbicide of the present invention is used in the form of a dust, generally, the dust can be prepared by mixing 1 to 15% by weight of the triketone derivative and/or the salt thereof, provided by the present invention, 80 to 97% by weight of a solid carrier and 2 to 5% by weight of a surfactant. Further, when the herbicide of the present invention is used in the form of granules, the granules can be prepared by mixing 1 to 15% by weight of the triketone derivative or the salt thereof, provided by the present invention, 80 to 97% by weight of a sold carrier and 2 to 5% by weight of a surfactant.

The above solid carrier is selected from mineral powders. Examples of the mineral powders include oxides such as diatomaceous earth and slaked lime, phosphates such as apatite, sulfates such as gypsum and silicates such as talc, pyrophyllite, clay, kaolin, bentonite, acidic terra alba, white carbon, powdered quartz and powdered silica.

The solvent is selected from organic solvents. Specific examples of the solvent include aromatic hydrocarbons such as benzene, toluene and xylene, chlorinated hydrocarbons such as o-chlorotoluene, trichloroethane and trichloroethylene, alcohols such as cyclohexanol, amyl alcohol and ethylene glycol, ketones such as isophorone, cyclohexanone and cyclohexenyl-cyclohexanone, ethers such as butyl cellosolve, diethyl ether and methyl ethyl ether, esters such as isopropyl acetate, benzyl acetate and methyl phthalate, amides such as dimethylformamide, and mixtures of these.

The surfactant is selected from anionic surfactants, non-ionic surfactants, cationic surfactants and amphoteric surfactants (such as amino acid and betaine).

Together with the triketone derivative of the general formula (I) and/or the salt thereof, the herbicide of the present invention may contain other herbicidally active ingredient as required. The other herbicidally active ingredient can be properly selected from known herbicides such as phenoxy-based, diphenyl ether-based, triazine-based, urea-based, carbamate-based, thiol carbamate-based, acid anilide-based, pyrazole-based, phosphoric acid-based, sulfonyl urea-based and oxadiazone-based herbicides.

Further, the herbicide of the present invention may contain an insecticide, a fungicide, a plant growth regulator and a fertilizer as required.

The present invention will be explained more in detail with reference to Examples hereinafter, while the present invention shall not be limited to these Examples.

PREPARATION EXAMPLE 1

Synthesis of 4,4,5,8-tetramethyl-6-(1,3-dioxycylohexan-2-yl)-carbonylthiochroman-1,1-dioxide (Compound No. 1)

3.0 Grams (0.01 mol) of 4,4,5,8-tetramethylthiochroman-6-carboxylic acid-1,1-dioxide (corresponding to compound of the general formula (II)) and 1.23 g (0.011 mol) of cyclohexane-1,3-dione (corresponding to compound of the general formula (III)) were mixed in 30 ml of acetonitrile, and to this mixture was added 2.27 g (0.011 mol) of DCC as a dehydrating agent at room temperature. After 8 hours, 1.6 g (0.015 mol) of triethylamine and 0.1 ml of acetone cyanohydrin were added to the reaction mixture, and the mixture was further allowed to react for 8 hours. After the completion of the reaction, acetonitrile was distilled off, and ethyl acetate and a 5% sodium carbonate aqueous solution were added. And, an insoluble was removed by filtration, and the residue was separated into two phases. The resultant aqueous phase was neutralized with hydrochloric acid, and a precipitate was recovered by filtration and dried to give 5.9 g (yield 64%) of the end product (Compound No. 1).

PREPARATION EXAMPLES 2–8

Compounds Nos. 2 to 8 shown in the right column of Table 1 were obtained in the same manner as in Preparation Example 1 except that the cyclohexane-1,3-dione corresponding to the compound of the general formula (III) was replaced with a compound shown in the left column of Table 1.

Table 1 shows the compounds used as raw materials in Preparation Examples 2 to 8, corresponding to the compound of the general formula (III), and the structural formulae and yields of obtained compounds. Table 2 shows the physical property data of the obtained compounds.

TABLE 1

| Pre. Ex. | Raw material | Compound No. | Structural formula | Yield (%) |
|---|---|---|---|---|
| 1 | (cyclohexane-1,3-dione) | 1 | (structure) | 64 |
| 2 | (5,5-dimethylcyclohexane-1,3-dione) | 2 | (structure) | 47 |

TABLE 1-continued

| Pre. Ex. | Raw material | Compound No. | Structural formula | Yield (%) |
|---|---|---|---|---|
| 3 | (5,5-dimethylcyclohexane-1,3-dione) | 3 | (structure) | 42 |
| 4 | (5-isopropylcyclohexane-1,3-dione) | 4 | (structure) | 27 |
| 5 | (5-phenylcyclohexane-1,3-dione) | 5 | (structure) | 31 |
| 6 | (cyclopentane-1,3-dione) | 6 | (structure) | 36 |
| 7 | (6-methyltetrahydro-2H-pyran-2,4-dione) | 7 | (structure) | 25 |
| 8 | (6-methyl-2H-pyran-2,4(3H)-dione) | 8 | (structure) | 42 |

TABLE 2

| Pre. Ex. No. | Compound No. | N.M.R. (ppm), Internal standard: Tetramethylsilane Solvent: Deutero chloroform | I.R. (cm$^{-1}$) KBr tablet method | Melting point |
|---|---|---|---|---|
| 1 | 1 | 1.55(6H, s) 1.90–2.20(2H, m) 2.30–2.60(3H, m) 2.35(3H, s) 2.65–2.90(3H, m) 2.75(3H, s) 3.30–3.60(2H, m) 6.80(H, s) | 2450, 2950 1680, 1280 1110 | 195.6–198.2 |
| 2 | 2 | 1.10–1.50(8H, m) 1.55(6H, s) 1.70–2.00(2H, m) 2.20–2.80(2H, m) 2.35(3H, s) 2.75(3H, s) 3.30–3.60(2H, m) 6.80(H, s) | 3500, 2950, 1680, 1300, 1130 | Glasslike substance |
| 3 | 3 | 1.10(6H, s) 1.55(6H, s) 2.10–2.90(6H, m) 2.35(3H, s) 2.75(3H, s) 3.30–3.60(2H, m) | 3500, 3000, 1690, 1300, 1120 | Glasslike substance |
| 4 | 4 | 1.00(6H, d) 1.55(6H, s) 2.00–2.80(8H, m) 2.35(3H, s) 2.75(3H, s) 3.30–3.50(2H, m) 6.80(H, s) | 2950, 1680, 1280, 1120 | Glasslike substance |
| 5 | 5 | 1.60(6H, s) 2.20–3.10(7H, m) 2.35(3H, s) 2.75(3H, s) 6.80(H, s) 7.70–7.60(5H, m) | 3450, 2950, 1600, 1300, 1120 | Glasslike substance |
| 6 | 6 | 1.55(6H, s) 2.20–2.80(6H, m) 2.40(3H, s) 2.75(3H, s) 3.30–3.50(2H, m) 6.95(H, s) | 3450, 2950, 1730, 1630, 1570, 1290, 1130 | Glasslike substance |
| 7 | 7 | 1.45(3H, s) 1.55(6H, s) 2.20–2.50(2H, m) 2.40(3H, s) 2.60–2.90(3H, m) 2.75(3H, s) 3.30–3.60(2H, m) 4.60(H, q) 6.85(H, s) | 3450, 2950, 1730, 1280, 1120 | Glasslike substance |
| 8 | 8 | 1.55(6H, s) 2.25(3H, s) 2.20–2.60(2H, m) 2.40(3H, s) 2.75(3H, s) 3.30–3.60(2H, m) 6.10(H, s) 6.85(H, s) | 2950, 1740, 1290, 1120 | 253.8–255.8 |

HERBICIDE EXAMPLES

(1) Preparation of Herbicide

97 Parts by weight of talc (trade name: Zeaklite) as a carrier, 1.5 parts by weight of alkylarylsulfonic acid (trade name: Neoplex, supplied by Kao-Atlas K.K.) as a surfactant and 1.5 parts by weight of a mixture of nonionic and anionic surfactants (trade name: Sorpol 800A, supplied by Toho Chemical Co., Ltd.) were uniformly pulverized and mixed to prepare a carrier for a wettable powder.

90 Parts by weight of the above carrier and 10 parts by weight of one of the compounds obtained in the above Preparation Examples 1~8 were uniformly pulverized and mixed to obtain herbicides.

(2) Foliar Treatment Test

Seeds of cocklebur, velvetleaf, pale smartweed, Jimsonweed, black nightshade, barnyardgrass and large crabgrass and seeds of corn were sown in 1/5,000-are Wagner pots filled with upland soil, and covered with upland soil. Then, the seeds were grown in a greenhouse. When these plants were at their one and two-leaved stage, a predetermined amount of the herbicide obtained in the above (1) was suspended in water and uniformly sprayed to their leaves and stalks at a gdosage of 2,000 liters/hectare. Thereafter, the plants were grown in the greenhouse, and 20 days after the treatment, the herbicide was evaluated for herbicidal efficacy and phytotoxicity to the crop. Table 3 shows the results.

The herbicidal efficacy and the phytotoxicity to the crop are shown as follows.

(Ratings)

| Herbicidal efficacy | Ratio of remaining plant weight to non-treated (%) |
|---|---|
| 0 | 81–100 |
| 1 | 61–80 |
| 2 | 41–60 |
| 3 | 21–40 |
| 4 | 1–20 |

| Phytotoxicity to crop | Ratio of remaining plant weight to non-treated (%) |
|---|---|
| − | 100 |
| ± | 95–99 |
| + | 90–94 |
| ++ | 80–89 |
| +++ | 0–79 |

The ratio of remaining plant weight to non-treated was determined as a ratio of remaining plant weight to non-treated=(remaining plant weight in treated plot/remaining plant weight in non-treated plot)×100.

(3) Upland Soil Treatment Test

Seeds of cocklebur, velvetleaf, pale smartweed, Jimsonweed, black nightshade, barnyardgrass and large crabgrass and seeds of corn were sown in 1/5,000-are Wagner pots filled with upland soil, and covered with upland soil. Then, a predetermined amount of the herbicide obtained in the above (1) was suspended in water and uniformly sprayed onto the soil surface. Thereafter, the plants were grown in the greenhouse, and 20 days after the treatment, the herbicide was evaluated for herbicidal efficacy and phytotoxicity to the crop. Table 4 shows the results.

The herbicidal efficacy and the phytotoxicity to the crop are shown on the basis of the ratings shown in (2) Foliar Treatment Test.

TABLE 3

| No. | Compound used | Dosage (g$^{a.i}$/ha) | Herbicidal efficacy | | | |
|---|---|---|---|---|---|---|
| | | | Cockle-bur | Velvet-leaf | Pale smart-weed | Jimson-weed |
| HeEx. 1 | 1 | 300 | 5 | 5 | 5 | 5 |
| HeEx. 2 | 2 | 300 | 5 | 4 | 5 | 5 |
| HeEx. 3 | 3 | 300 | 5 | 5 | 5 | 5 |
| HeEx. 4 | 7 | 300 | 3 | 3 | 5 | 5 |

| No. | Compound used | Dosage (g$^{a.i}$/ha) | Herbicidal efficacy | | | Phytotoxicity to crop Corn |
|---|---|---|---|---|---|---|
| | | | Black night-shade | barn-yard-grass | Large crab-grass | |
| HeEx. 1 | 1 | 300 | 5 | 3 | 5 | — |
| HeEx. 2 | 2 | 300 | 5 | 5 | 3 | — |
| HeEx. 3 | 3 | 300 | 5 | 5 | 3 | — |
| HeEx. 4 | 7 | 300 | 5 | 2 | 2 | — | a.i. = active ingredient
HeEx. = Herbicide Example

TABLE 4

| No. | Compound used | Dosage (g$^{a.i}$/ha) | Herbicidal efficacy | | | |
|---|---|---|---|---|---|---|
| | | | Cockle-bur | Velvet-leaf | Pale smart-weed | Jimson-weed |
| HeEx. 5 | 1 | 300 | — | 5 | 5 | 5 |
| HeEx. 6 | 2 | 300 | — | 4 | 5 | 5 |
| HeEx. 7 | 3 | 300 | — | 5 | 5 | 5 |
| HeEx. 8 | 7 | 300 | — | 5 | 5 | 5 |
| HeEx. 9 | 8 | 300 | — | 5 | 5 | 5 |

| No. | Compound used | Dosage (g$^{a.i}$/ha) | Herbicidal efficacy | | | Phytotoxicity to crop Corn |
|---|---|---|---|---|---|---|
| | | | Black night-shade | barn-yard-grass | Large crab-grass | |
| HeEx. 5 | 1 | 300 | 3 | 4 | 4 | — |
| HeEx. 6 | 2 | 300 | 5 | 5 | 2 | — |
| HeEx. 7 | 3 | 300 | 5 | 2 | 3 | — |
| HeEx. 8 | 7 | 300 | 5 | 2 | 2 | — |
| HeEx. 9 | 8 | 300 | 5 | 3 | 4 | — | a.i. = active ingredient
HeEx. = Herbicide Example

Tables 3 and 4 show that the triketone derivative of the present invention can control a broad range of upland weeds at a low dosage without causing phytotoxicity on corn.

According to the present invention, there is provided a novel triketone derivative which can control a broad range of upland weeds at a low dosage without causing phytotoxicity on corn, and a herbicide containing the same as an active ingredient.

We claim:

1. A triketone compound of the formula (I)

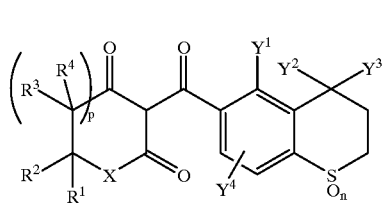

(I)

wherein
$Y^1$ is a $C_1$ to $C_4$ alkyl group, a halogen atom or a $C_1$ to $C_4$ haloalkyl group,
each of $Y^2$ and $Y^3$ is independently a $C_1$ to $C_4$ alkyl group,
$Y^4$ is a hydrogen atom, a $C_1$ to $C_4$ alkyl group or a halogen atom,
n is an integer of 0, 1 or 2,
p is 0 or 1,
each of $R^1$, $R^2$, $R^3$ and $R^4$ is independently a hydrogen atom, a $C_1$ to $C_4$ alkyl group or a phenyl group, or when p is 1, either $R^1$ or $R^2$ and either $R^3$ or $R^4$ optionally bond to each other to form an intramolecular double bond, and
X is an oxygen atom or a sulfur atom.

2. The triketone compound of claim 1, wherein $Y^1, Y^2, Y^3$ and $Y^4$ is independently methyl.

3. The triketone compound of claim 1, wherein $Y^4$ is substituted at 8-position of the thiochromane ring.

4. The triketone compound of claim 1, wherein n is 2.

5. The triketone compound of claim 1, wherein each of $R^1, R^2, R^3$ and $R^4$ is independently a hydrogen atom, methyl, i-propyl or phenyl, or when p is 1 and either $R^1$ or $R^2$ and either $R^3$ or $R^4$ optionally bond to each other to form an intramolecular double bond.

6. The triketone compound of claim 1, wherein X is an oxygen atom

7. A herbicidal composition containing, as an active ingredient, an effective herbicidal amount of the triketone compound recited in claim 1 and a carrier.

8. The herbicide composition of claim 7, which further comprises at least one member selected from the group consisting of phenoxy-based, diphenyl ether-based, a triazine-based, urea-based, carbamate-based, a thiolcarbamate-based, acid anilide-based, a pyrazole-based, phosphoric acid-based, sulfonyl urea-based, and oxadiazone-based herbicides.

9. The herbicide composition of claim 7, which further comprises at least one member selected from an insecticide, a fungicide, a plant growth regulator and a fertilizer.

10. The triketone compound of claim 1, wherein
$Y^1$ is methyl, a chlorine atom or —$CF_3$;
$Y^2$ is methyl; $Y^3$ is methyl; $Y^4$ is a hydrogen atom, methyl or a fluorine atom; each of $R^1$, $R^2$, $R^3$ and $R^4$ is independently a hydrogen atom, methyl, 1-propyl or a phenyl group.

11. The triketone compound of claim 10, wherein $Y^1$ is methyl, $Y^2$ is methyl, $Y^3$ is methyl and $Y^4$ is methyl.

12. The triketone compound of claim 1, wherein p is 1 and either $R^1$ or $R^2$ and either $R^3$ or $R^4$ bond to each other to form an intramolecular double bond.

13. The triketone compound of claim 12, wherein $Y^1$ is methyl, $Y^2$ is methyl, $Y^3$ is methyl and $Y^4$ is methyl.

14. The triketone compound of claim 1, wherein the compound is of the formula

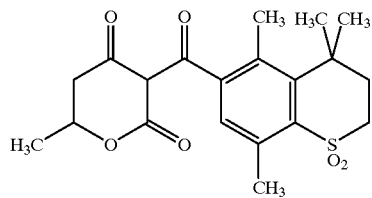

15. The triketone compound of claim 1, wherein the compound is of the formula

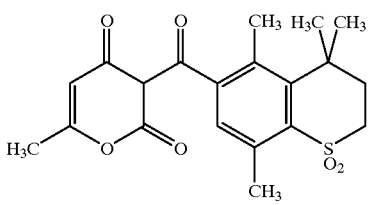

16. A method for combatting weeds comprising applying to weeds or to a locus thereof an effective herbicidal amount of the compound of claim 1, alone or in combination with a carrier.

* * * * *